United States Patent
Adler et al.

(10) Patent No.: US 9,180,282 B2
(45) Date of Patent: Nov. 10, 2015

(54) IMPLANTABLE DRUG DELIVERY SYSTEM HAVING PERIODIC DRUG DELIVERY REGIMEN TO AVOID GRANULOMAS

(75) Inventors: Steven C. Adler, Randolph, NJ (US); Paul Burke, Bellingham, MA (US)

(73) Assignee: FLOWONIX MEDICAL INCORPORATED, Mount Olive, NJ (US)

(*) Notice: Subject to any disclaimer, the term of this patent is extended or adjusted under 35 U.S.C. 154(b) by 752 days.

(21) Appl. No.: 12/555,257

(22) Filed: Sep. 8, 2009

(65) Prior Publication Data
US 2010/0152713 A1    Jun. 17, 2010

Related U.S. Application Data

(60) Provisional application No. 61/094,449, filed on Sep. 5, 2008.

(51) Int. Cl.
*A61K 9/22* (2006.01)
*A61M 31/00* (2006.01)
*A61M 5/142* (2006.01)

(52) U.S. Cl.
CPC ......... *A61M 31/002* (2013.01); *A61M 5/14276* (2013.01); *A61M 2205/50* (2013.01)

(58) Field of Classification Search
CPC .................. A61M 5/14276; A61M 2205/3523; A61M 2005/14208; A61M 5/16877; A61M 2205/50; A61M 2025/007
USPC .......... 604/890.1, 891.1, 506, 500, 892.1, 66; 607/3
See application file for complete search history.

(56) References Cited

U.S. PATENT DOCUMENTS

| 5,954,058 | A | 9/1999 | Flaherty |
| 6,231,560 | B1* | 5/2001 | Bui et al. ...................... 604/500 |
| 6,764,472 | B1 | 7/2004 | Burke et al. |
| 7,083,593 | B2 | 8/2006 | Stultz |
| 7,108,686 | B2 | 9/2006 | Burke et al. |
| 2002/0156462 | A1* | 10/2002 | Stultz ........................ 604/891.1 |

(Continued)

OTHER PUBLICATIONS

Deer et al. Management of Intrathecal Catheter-Tip Inflammatory Masses: An Updated 2007 Consensus Statement From an Expert Panel. Neuromodulation: Technology at the Neural Interface. vol. 11, Issue 2: pp. 77-91. Published Online: Apr. 2, 2008.*

(Continued)

*Primary Examiner* — Nicholas Lucchesi
*Assistant Examiner* — Gerald Landry, II
(74) *Attorney, Agent, or Firm* — The Marbury Law Group, PLLC

(57) ABSTRACT

An implantable drug delivery system including: a biocompatible or bio-inert housing containing a drug infusion pump, a drug chamber from which a liquid drug is dispensed when the pump applies a force to the drug chamber, and an internal controller actuating the pump; a delivery catheter extending from the housing to one or more drug delivery treatment sites in a target tissue, wherein the catheter includes a lumen having an inlet to receive a drug pumped from the drug chamber and an outlet are positioned at the target tissue, wherein the drug flows through the outlet to the target tissue, and wherein the internal controller stores and executes an automatic periodic flow regimen which commands the pump and drug chamber to periodically dispense an intermittent bolus or pulse of the liquid drug, wherein the periodic flow regimen provides a prophylactic treatment for granuloma.

8 Claims, 3 Drawing Sheets

(56) References Cited

U.S. PATENT DOCUMENTS

| | | | |
|---|---|---|---|
| 2003/0040479 A1* | 2/2003 | Demopulos | A61K 31/4436 514/18.4 |
| 2004/0015154 A1 | 1/2004 | Harper et al. | |
| 2004/0138562 A1* | 7/2004 | Makower | A61M 25/0084 600/439 |
| 2005/0090549 A1* | 4/2005 | Hildebrand et al. | 514/561 |
| 2005/0113745 A1 | 5/2005 | Stultz | |
| 2005/0192638 A1* | 9/2005 | Gelfand et al. | 607/3 |
| 2006/0264897 A1* | 11/2006 | Lobl | A61M 39/0208 604/506 |
| 2008/0061961 A1* | 3/2008 | John | A61B 5/4809 340/539.12 |
| 2008/0154215 A1 | 6/2008 | Rosenberg et al. | |
| 2009/0221956 A1* | 9/2009 | Abrams | A61M 5/14276 604/66 |
| 2009/0234302 A1* | 9/2009 | Hoendervoogt | A61M 5/14276 604/288.01 |

OTHER PUBLICATIONS

Timothy Deer, MD, et al., "Management of Intrathecal Catheter-Tip Inflammatory Masses: An Updated 2007 Consensus Statement From an Expert Panel," International Neuromodulation Society, Neuromodulation: Technology at the Neural Interface, vol. 11, No. 2, 2008, pp. 77-91.

Inset Technologies Inc., User Manual, "Prometra Programmer—For use with Prometra Programmable Pump," Mar. 2008, pp. 1-60.

* cited by examiner

IMPLANTABLE DRUG DELIVERY SYSTEM HAVING PERIODIC DRUG DELIVERY REGIMEN TO AVOID GRANULOMAS

CROSS RELATED APPLICATION

This application claims priority to provisional application Ser. No. 61/094,449 filed Sep. 5, 2008.

BACKGROUND OF THE INVENTION

The invention relates generally to implantable drug delivery systems and, particularly, to an implantable pump having a controller regulating the delivery of the drug.

Implantable drug delivery systems infuse drugs to tissue treatment sites inside of patients. For example, morphine is delivered to a spinal cord region by implanted drug delivery systems to provide long term pain relief to patients suffering chronic pain. Conventional wisdom teaches that drugs for chronic pain are to be infused at a continual rate to provide uniform and steady drug delivery to the treatment sites. Accordingly, implantable drug delivery systems are programmed or otherwise configured to deliver drug in a constant flow fashion.

However, granuloma can arise around the catheters associated with implanted drug delivery systems. Granuloma formation is typically an inflammatory tissue mass that forms around the catheter. A granuloma formation near a spinal cord may press on the cord and cause neurological side-effects. Catheters to deliver morphine are typically positioned near the spinal cord in patients. There is a need to reduce the risk of granuloma formation associated with implantable morphine drug delivery systems.

Granuloma formation at catheter tips is discussed in Deer et al, "Management of Intrathecal Catheter-Tip Inflammatory Masses: An Updated 2007 Consensus Statement From An Expert Panel" (Neuromodulation: Technology at the Neural Interface, Vol. 11, No. 2, 2008) ("Deer Article") which reports the results of an expert panel that considered granulomas caused by intrathecal (IT) therapies, where IT refers to injections into the spinal canal. The Deer Article at page 86 states that "granulomas are most likely a function of drug dose, drug concentrations, a combination of the two, the way the drug is delivered and/or CSF [cerebrospinal fluid] flow rate." Also, the Deer Article at page 86 reports that "[m]ost panelists thought that there does exist a difference, theoretically at least, in the rate of granuloma formation caused by bolus infusion vs. continuous infusions through the catheter . . . . However, the panel did also feel that frequent repeated boluses of high-concentration opioid medications might potentially lead to a similar proinflammatory effect as continuous infusions." Further, the Deer Article at page 87 reports that consideration as given to prophylactic measures that might prevent granulomas including "using bolus dosing instead of slow continuous infusion, minimizing concentration/dose of the agent infused (e.g., especially of morphine sulfate and hydromorphone) to the daily dose limits proposed by the Consensus Panel, avoiding ultra slow flow rates and/or delivering the drug into larger CSF space over the spinal cord."

The recommendations for preventing granuloma formation stated in the Deer Article at page 89 include: "minimize concentrations and doses of intrathecal (IT) agents, especially of morphine sulfate and hydromorphone" and "avoid ultra-slow flow rates." The reported recommendations do not include intermittent bolus drug delivery.

BRIEF DESCRIPTION OF THE INVENTION

An implantable drug delivery system has been developed that applies an automatic and intermittent pulse or bolus of drug, where the intermittent pulse or bolus is a prophylactic treatment to avoid granulomas. For example, a morphine based drug is automatically delivered every few hours by an implanted drug dispensing pump to a treatment site at or near the spinal canal. The inventors believe that an automatic and periodic delivery of drugs will provide effective therapeutic treatment, such as chronic pain relief, that is as effective as the conventional constant flow of drugs. The intermittent drug flow should also lower the risk of granuloma formation at the treatment site and, especially, at a spinal canal treatment site.

A controller in the implanted drug delivery is programmed with a flow regimen that causes the system to automatically pump an intermittent pulse or bolus of drug, such as every four hours, to the treatment site. The automatic flow regimen may be adjusted or otherwise reprogrammed by a physician or other health care clinician using an external controller that communicates with an internal controller in the implanted drug delivery system. For example, the flow regime may be adjusted to change the dosage or the timing of the drug bolus of morphine would be delivered over each twenty-four (24) hour period.

In one embodiment, the implantable drug delivery system includes: a biocompatible or bio-inert housing containing a drug infusion pump, a drug chamber from which a liquid drug is dispensed when the pump applies a force to the drug chamber, and an internal controller actuating the pump; a delivery catheter extending from the housing to one or more drug delivery treatment sites in a target tissue, wherein the catheter includes a lumen having an inlet to receive a drug pumped from the drug chamber and an outlet are positioned at the target tissue, wherein the drug flows through the outlet to the target tissue, and wherein the internal controller stores and executes an automatic periodic flow regimen which commands the pump and drug chamber to periodically dispense an intermittent bolus or pulse of the liquid drug, wherein the periodic flow regimen provides a prophylactic treatment for granuloma.

Further, a method has been developed for automatically dispensing a drug from an implantable drug delivery system having a biocompatible or bio-inert housing containing a drug infusion pump, a drug chamber, and an internal controller actuating the pump, and a delivery catheter, the method comprising: programming a drug delivery regime for automatic drug infusion into the controller, wherein the drug delivery regime includes a periodic drug dispensing schedule to provide a prophylactic treatment to avoid granulomas proximate to the target tissue; positioning the delivery catheter to a target tissue in a mammalian patient; executing by the controller the drug delivery regime to periodically actuate the drug infusion pump to periodically discharge a bolus or pulse of a liquid containing the drug from the drug chamber and into the delivery catheter, and periodically and automatically delivering the bolus or pulse of the liquid containing the drug to the target tissue.

DETAILED DESCRIPTION OF THE INVENTION

Figure 1:
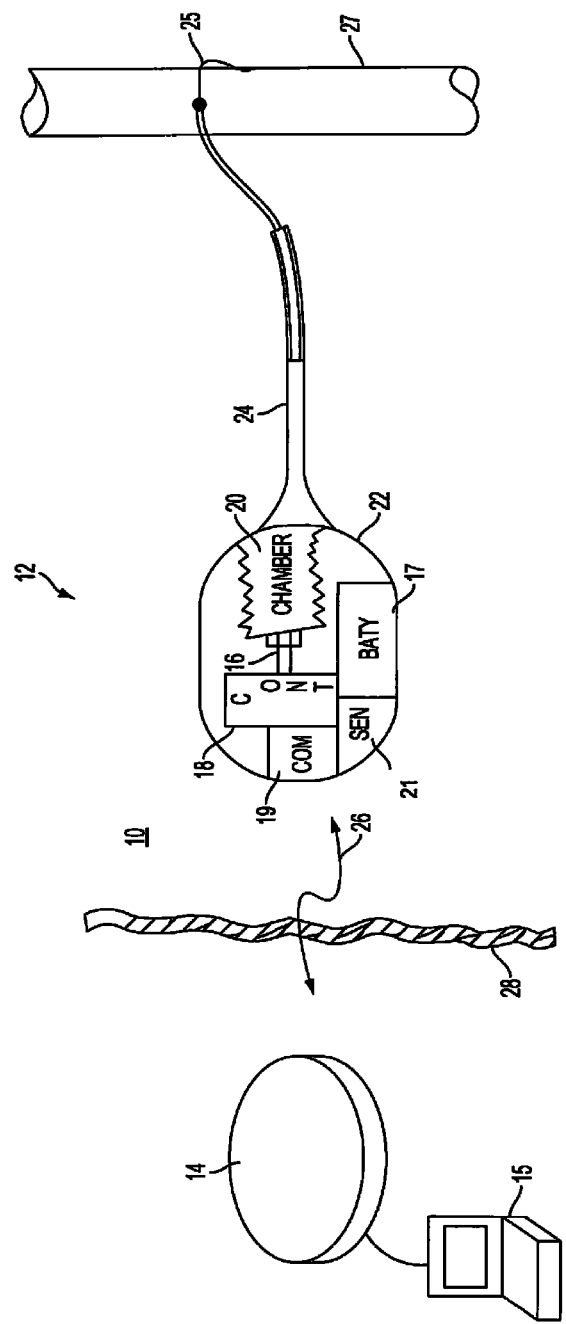
FIG. 1 is a schematic diagram showing a patient with an implantable drug delivery system and an external controller for reprogramming the drug delivery system internal to the patient.

FIG. 1 is a schematic diagram showing a patient 10 with an implantable drug delivery system 12 and an external controller 14 for reprogramming the drug delivery system while inside the patient, such as a mammalian subject and specifically a human.

The implantable drug delivery system 12 typically includes a drug infusion pump 16, a battery 17, an internal computer controller 18, a communication module 19 to provide wireless communication with the controller 18 and a wireless recharging link, a drug chamber(s) 20, one or more sensors 21 and a biocompatible or bio-inert housing 22 for these components. The system 12 may be implanted subdermally, with a local outlet, or with a delivery (infusion) catheter 24 extending from the pump to one or more drug delivery treatment sites 25 in target tissue, e.g., the spinal canal 27, of the patient. The infusion catheter 24 receives drug(s) pumped from the drug chamber(s) into a lumen(s) of the catheter. The outlet(s) of the lumen(s) are positioned at a target site(s) in the patient. Some or all of the components of the implantable drug delivery system 12 are partly or wholly implanted within the body of an individual.

The drug delivery system infuses a drug, e.g., a liquid including a medicament such as morphine, to a treatment site adjacent one or more outlets in a distal portion of the delivery catheter 24. The drug is pumped from the drug chamber 20 into an inlet portion at a proximal portion of the delivery catheter. The catheter is attached to the housing 22 and the inlet portion of the catheter is arranged to receive the drug from the drug chamber. The drug infusion pump 16 applies a pressure to the drug in the drug chamber or otherwise applies a motive force to the drug to force the drug from the chamber into the inlet to the delivery catheter. For example, the chamber is collapsible and the pump progressively reduces the volume of the chamber to infuse drug into the catheter. Once the pump is activated, fluid containing the drug moves from the chamber 20 through the delivery catheter and is released into tissue at the target site 27.

The pump is powered by the battery 17 and is operated by the internal computer controller 18. The sensors 21 provide data to the controller 18 regarding physiological conditions of the patient, such as body temperature, heart rate and a manual input, such as a subdermal implant that allows a user to manually request an increase or decrease of the dosage or rate of drug delivery.

Figure 2:
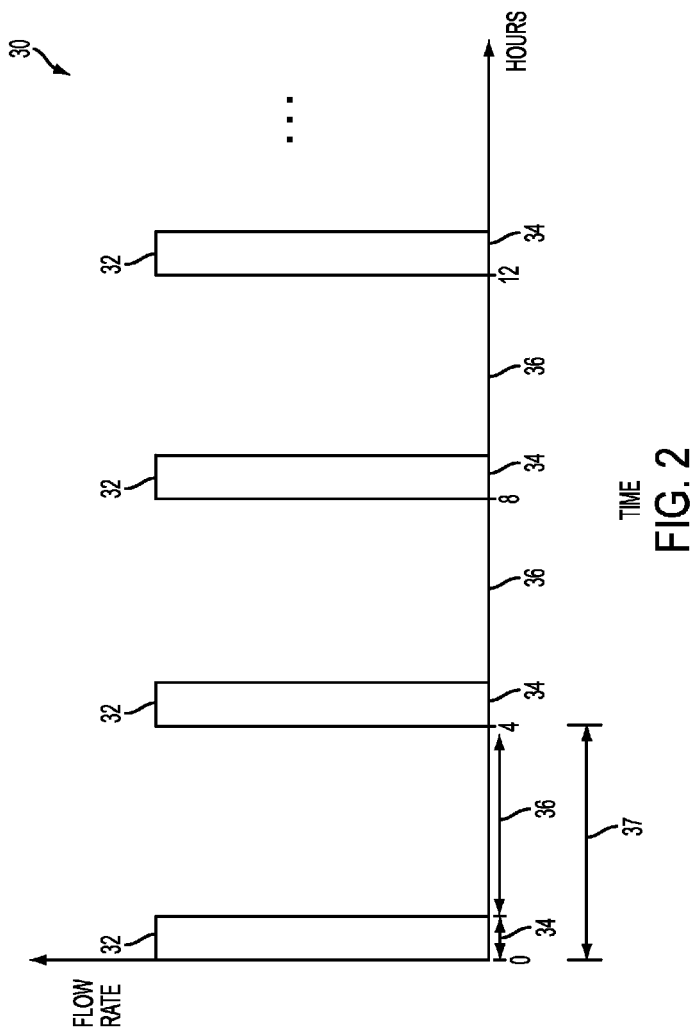
FIG. 2 is an exemplary drug delivery timing protocol for a periodic drug flow regimen.

The internal computer controller 18, e.g., a microprocessor with associated electronic memory, operates the drug delivery system, e.g., actuates the pump 16 based on the control regimes, e.g., codes and commands stored as software in electronic memory of the internal computer controller 18. The control regimes are applied by the controller 18 to activate the fluid pump so as to automatically dispense the drug from the drug chamber 20 in accordance with a prescribed duration, flow rate or other parameters of drug delivery prescribed by the drug flow regimen 30 (FIG. 2). The controller 18 receives data from the sensors 21 and may use the sensor data to adjust, start or terminate the delivery of drugs. The manner in which the controller responds to sensor data will typically be prescribed in the control regimes. Further, the controller communicates with the communication module 19 to receive changes to the control regimes and software updates and to send data regarding the drug delivery system, such as amount of drug that has been dispensed and a history of dosage and periodic rate of drug delivery.

The control regime for drug infusion includes control information that prescribes an amount(s) of drug to be dispensed, e.g., the dosage, a schedule for dispensing the drug and other information needed by the controller to regulate the infusion of the drug to the treatment site. The control information may be based on a drug prescription prepared by a physician and communicated to the internal controller 18 from the external controller 14.

The external controller 14 communicates 26 with the internal computer controller 18 to reprogram, adjust or collect data from the control regimes and drug delivery data stored in that internal controller. Further, the external controller, which may include a separate charger, recharges the battery 17. The external controller 14 is positioned on skin tissue 29 of the patient that is proximate the implanted drug delivery system 12. The external controller 14 includes a wireless transceiver which communicates data, control commands and programs, e.g., drug delivery flow regimens, with the communication module 19 in the housing 22. Further, the external controller 14 includes a user interface 15, such as a display and a keyboard or keypad, to allow a physician, or other health care professional, to make selections regarding the drug flow regimen, such as dosages and a periodic rate of the dosages.

FIG. 2 is an exemplary drug delivery timing protocol for an automatic and periodic drug flow regimen 30. The automatic, periodic drug flow regimen 30 delivers medication in a sequence of periodic drug infusions 34 at the treatment site. The control regime 30 schedules the timing of the periodic application of a bolus or pulse 32 of a drug, where the bolus or pulse may be delivered at a particular flow rate such as up to 1.2 milliliter per hour (mL/hr). The control regime specifies the cycle time, e.g., every four hours, for delivery of a bolus or pulse 32 of the drug and the duration of each bolus or pulse. The bolus or pulse 32 may be dispensed at a steady flow rate by the pump and from the chamber, or may be dispensed in a gradually increasing flow rate followed by a gradually decreasing flow rate of the drug in the bolus or pulse.

The drug delivery cycle 37 includes a first period 34 that includes the bolus or pulse 32 and a second period 36 during which no drug is infused to the treatment site. The cycle 37 is repeated continuously for a prescribed period, e.g., seven days, or until the internal controller determines that an insufficient amount of drug remains in the chamber 20. The drug delivery cycle 37 may be between one to twenty-four hours, more preferably between three to five hours, and most preferably four hours. Further, the duration of the first period 34 in each cycle may be between one minute to 24 minutes and may be determined to provide an fluid infusion rate at the treatment site that delivers an amount of drug at an acceptable drug infusion rate. During first period 34, the controller 18 actuates the drug infusion pump 16 to pump a drug solution from the drug chamber 20 into the catheter 24 and to the treatment site 25.

It is proposed that extended periods 36 of no drug delivery between first periods 34 of relatively short bursts of a drug bolus or pulse will avoid or minimize granulomas, particularly for delivery of morphine to treatment sites at or near the spinal canal. Further, it is proposed that the delivery of drugs, such as morphine, by a bolus or pulse will achieve substantially the same beneficial therapeutic results as a continuous flow of drug to the treatment site.

The second period 36 in each drug delivery cycle 37 may be more than 3.5 hours and defines a period during which no drug is infused from the catheter to the treatment site. The second period 36 of no drug infusion may be five to twenty times longer in duration than the first period 34 of drug infusion. The second period 36 is determined by balancing the timing of the dissipation of the therapeutic effect, e.g., pain relief, resulting from the infusion of a drug bolus or pulse and the period of non-drug infusion needed to avoid granuloma. The balance of the timing may be determined by experimentation and appears to be dependent on the drug composition, concentration and flow rate.

Figure 3:
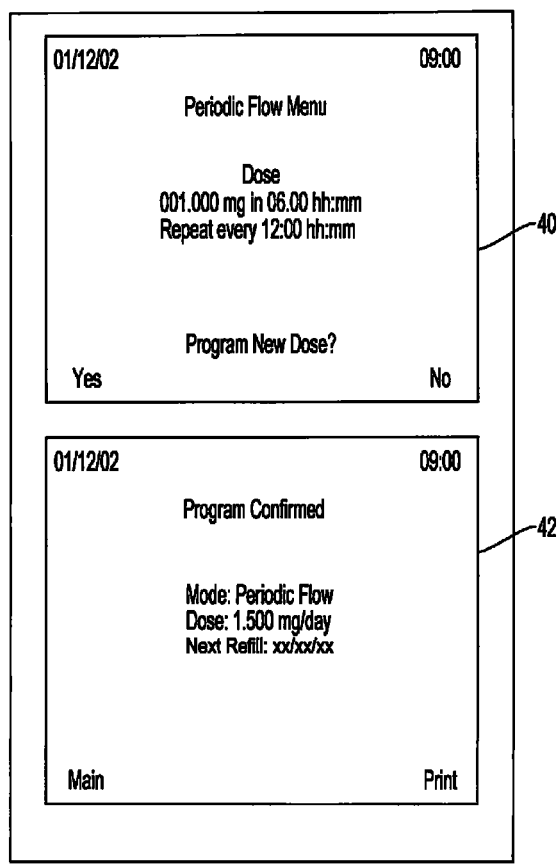
FIG. 3 are exemplary screen displays of the external controller showing a prescribed periodic flow for prescribing intermittent bolus dosing of a drug.

FIG. 3 are exemplary screen displays 40, 42 presented by the user interface 15 of the external controller 14. The screen displays show information regarding a periodic flow for prescribing intermittent bolus dosing of a drug and associated control settings. The screen shows the date and time, an informative title, such as, "Periodic Flow Menu" or "Program Confirmed", information regarding the dose being inputted through the user interface, and available selections, such as "Program a New Dose . . . yes or no", and "main" (referring to a return to a main screen) or "print". The information regarding the dose being inputted may include: (i) the dosage amount, such as 1 mg to be delivered over a course of 6 hours or 0.5 mg in each bolus; (ii) mode: periodic flow or continuous flow (indicating whether there will be an intermittent bolus of or a continuous flow of a drug to the treatment site), (iii) the cycle rate (also referred to as repetition rate), such as every 12-hours, for the intermittent delivery of a drug bolus, (iv) the next refill date for the drug chamber (the chamber may be refilled by inserting a needle through the skin tissue 29 and into the chamber and infusing the drug through the needle and into the chamber), and (v) the duration of each bolus. Further, the controller 14, 18 may automatically establish certain settings, such as the duration of a bolus or that period between each bolus based on manually input values of the drug dosage, such as the dosage, e.g., 1.500 mg/day, to be delivered over a 24 hour period.

The automatic intermittent bolus dosage prescription, such as shown in FIG. 3, may be inputted to the user interface 15 of the external controller 14 in connection with refilling the drug in the chamber 20 of the implantable drug delivery system 12. Using the screens 40, 42, shown in FIG. 3, the periodic flow regimen is entered into the user interface 15. The external controller 14 is positioned adjacent the skin tissue 29 and starts a communication with the communication module 19 and internal controller 18 of the implanted drug delivery system. The external controller may alert, e.g. by audible tones, the physician when the communication has been established between the external and internal controllers. The physician may interact with the external controller to cause the desired prescription for drug delivery to be transmitted from the external controller to the internal controller and properly stored in the internal controller. The controllers may issue various audible alerts to indicate to the physician that changes to the drug flow regimen are properly entered to the internal controller.

Limits may be imposed on the periodic flow regimen and these limit may be stored in the internal and the external controllers 14, 18. The limits may be maximum and minimum settings for the programmed medication dosage, the time over which the dosage is delivered, and the interval at which the dosage is repeated. A exemplary set of limits is stated in Table 1 below:

TABLE 1

| | | Value Limit |
|---|---|---|
| Dose | Min | 000.000 mg |
| | Max | 999.999 mg |
| Pump Delivery Rate | Min | 0.0 mL/day during emergency pump stop |
| | | 0.1 mL/day to maintain catheter patency |
| | Max | 28.8 mL/day, or 1.2 mL/hr, or 20 mcL/min |
| Duration | Min | 1 min |
| | Max | 23:59 min |
| Repeat | Max | 24:00 hr |
| Single rate | Max | 1.2 mL/hr |
| Sum of all rates | Max | Daily Dose Limit, if programmed, OR 28.8 mL/day, if no Daily Dose Limit |
| Sum of all rate durations | = | 24 hr |

The limits stated in Table 1 are the minimum and maximum values that may be programmed into the computer controller 14, 18. A error may result if values outside the limits are entered in the controller 14. The limits provide a safety feature and may avoid a potentially unhealthy dosage or rate of drug delivery.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An implantable drug delivery system comprising:
a biocompatible or bio-inert housing containing a drug infusion pump, a drug chamber from which a liquid drug is dispensed when the pump applies a force to the drug chamber, and an internal controller actuating the pump;
a delivery catheter extending from the housing to one or more drug delivery treatment sites in a target tissue, wherein the catheter includes a lumen having an inlet to receive a drug pumped from the drug chamber and an outlet positioned at the target tissue, wherein the drug flows through the outlet to the target tissue, and
wherein the internal controller stores and executes an automatic periodic flow regimen which commands the pump and drug chamber to periodically dispense an intermittent bolus or pulse of the liquid drug, the periodic flow regimen including a drug delivery cycle having at least a first period of no drug infusion and a second period of drug delivery by the bolus or the pulse, wherein the first period is at least five times longer than the second period, wherein the periodic flow regimen provides a prophylactic treatment for granuloma, wherein the one or more drug delivery treatment sites is the spinal canal and the drug chamber contains a morphine based drug formulation, the implantable drug delivery system further comprising:
a memory; and
a processor coupled to the memory and configured with processor-executable commands to perform operations comprising:
receiving a drug dosage input value corresponding to a total quantity of the drug to be dispensed over a treatment period, wherein the treatment period is longer than the period of the drug delivery cycle; and
based on the received drug dosage input value, determining values corresponding to the first period of no drug infusion and the second period of drug delivery in the drug delivery cycle so as to provide the total quantity of the drug being dispensed over the treatment period as specified by the received drug dosage input value, wherein the value corresponding to the period of no drug infusion is determined based on a timing of a dissipation of the therapeutic effect resulting from the delivery by a bolus or pulse of the drug and a time period of no drug infusion needed to avoid granulomas proximate to the target tissue.

2. The implantable drug delivery system of claim 1 wherein the flow regimen includes a drug delivery cycle having at least a first period of no drug infusion and a second period of drug delivery by the bolus or the pulse, wherein the first period is at least five times longer than the second period and no more than twenty times longer than the second period.

3. A method for automatically dispensing a drug from an implantable drug delivery system having a biocompatible or bio-inert housing containing a drug infusion pump, a drug chamber, and an internal controller actuating the pump, and a delivery catheter, the method comprising:

receiving, at a controller, a drug dosage input value corresponding to a total quantity of the drug to be dispensed over a treatment period, wherein the treatment period is longer than a period of a drug delivery cycle;

based on the received drug dosage input value, determining values corresponding to a first period of no drug infusion and a second period of drug delivery in the drug delivery cycle so as to provide the total quantity of the drug being dispensed over the treatment period as specified by the received drug dosage input value, wherein the value corresponding to the period of no drug infusion is determined based on a timing of a dissipation of the therapeutic effect resulting from the delivery by a bolus or pulse of the drug and a time period of no drug infusion needed to avoid granulomas proximate to the target tissue;

programming a drug delivery regime for automatic drug infusion into the internal controller, wherein the drug delivery regime includes a periodic drug dispensing schedule comprising the drug delivery cycle having at least the first period of no drug infusion and the second period of drug delivery by a bolus or pulse of the liquid, wherein the first period is at least five times longer than the second period, to provide a prophylactic treatment to avoid granulomas proximate to a target tissue;

positioning the delivery catheter to one or more drug delivery treatment sites in a target tissue in a mammalian patient, wherein the one or more drug delivery treatment sites is the spinal canal and the drug chamber contains a morphine based drug formulation;

executing by the internal controller the drug delivery regime to periodically actuate the drug infusion pump to periodically discharge a bolus or pulse of a liquid containing the drug from the drug chamber and into the delivery catheter, and periodically and automatically delivering the bolus or pulse of the liquid containing the drug to the target tissue.

4. The method of claim 3 wherein the drug delivery regime regimen includes a drug delivery cycle having at least a first period of no drug infusion and a second period of drug delivery by the bolus or the pulse of the liquid, wherein the first period is at least five times longer than the second period and no more than twenty times longer than the second period.

5. The implantable drug delivery system of claim 1, wherein the first period of no drug infusion in the drug delivery cycle is greater than 3.5 hours.

6. The implantable drug delivery system of claim 1, wherein the second period of drug delivery in the drug delivery cycle is between 1 minute and 24 minutes.

7. The method of claim 3, wherein the first period of no drug infusion in the drug delivery cycle is greater than 3.5 hours.

8. The method of claim 3, wherein the second period of drug delivery in the drug delivery cycle is between 1 minute and 24 minutes.

* * * * *